United States Patent [19]

Heinsohn et al.

[11] Patent Number: 5,217,582
[45] Date of Patent: Jun. 8, 1993

[54] PROCESS FOR THE ISOLATION OF ALKYL GLYOXYLATE

[75] Inventors: George E. Heinsohn, Elkton, Md.; John F. Kook, Hockessin; John R. Kosak, Greenville, both of Del.; Rudolf E. Svadlenak, Sunriver, Oreg.

[73] Assignee: E. I. Du Pont de Nemours and Company, Wilmington, Del.

[21] Appl. No.: 830,576

[22] Filed: Feb. 7, 1992

Related U.S. Application Data

[63] Continuation-in-part of Ser. No. 686,275, Apr. 15, 1991, abandoned, which is a continuation of Ser. No. 540,914, Jun. 20, 1990, abandoned.

[51] Int. Cl.$^5$ .............................. B01D 3/14; C07C 69/66
[52] U.S. Cl. .............................. 203/78; 203/42; 203/43; 203/80; 203/84; 560/177; 560/186
[58] Field of Search .............................. 203/42, 43, 71, 73, 203/80, 78, 84, 57, 60, 64, 67, 98; 560/177, 186

[56] References Cited

U.S. PATENT DOCUMENTS

| | | | |
|---|---|---|---|
| 4,502,923 | 3/1985 | Dyroff et al. | 203/71 |
| 4,692,547 | 9/1987 | Driscoll et al. | 560/186 |
| 4,814,491 | 3/1989 | Driscoll et al. | 560/186 |
| 4,820,385 | 4/1989 | Cova et al. | 203/2 |
| 4,867,849 | 9/1989 | Cova et al. | 203/28 |

FOREIGN PATENT DOCUMENTS

1224216 7/1987 Canada .

Primary Examiner—Wilbur Bascomb, Jr.
Attorney, Agent, or Firm—Charles E. Krukiel

[57] ABSTRACT

A process is provided for separating high purity alkyl glycolate from a gaseous reaction mixture resulting from the catalyzed gas phase oxidation of alkyl glycolate. A hot solvent which is immiscible with water but selectively dissolves alkyl glycolate and alkyl glyoxylate is brought in contact with the gaseous reaction mixture, and water and alcohol vapors are removed from the hot solvent. The alkyl glyoxylate is removed from the solution by a first distillation and the alkyl glycolate and solvent are then separated in a second distillation.

20 Claims, No Drawings

PROCESS FOR THE ISOLATION OF ALKYL GLYOXYLATE

This application is a continuation-in-part of application Ser. No. 07/686,275, filed Apr. 15, 1991 (now abandoned.), which is a continuation of application Ser. No. 07/540,914, filed Jun. 20, 1990 (now abandoned).

BACKGROUND OF THE INVENTION

The present invention relates generally to an improved process for producing alkyl glyoxylates and, more particularly, to a process for separating an alkyl glyoxylate from the corresponding alkyl glycolate used to produce it and various other reaction constituents.

One method for producing alkyl glyoxylates is by the oxidative dehydrogenation of alkyl glycolates in the presence of a silver catalyst. For each mole of glyoxylate, one mole of water is produced. Additional water can be provided by side reactions, along with lesser amounts of the alcohol corresponding to the alkyl moiety of the glyoxylate and various other minor by-products. Product isolation is complicated by liquid phase reactions between the alkyl glyoxylate and unconverted glycolate or co-products (most notably hydroxyl species such as water and the alcohol corresponding to the alkyl moiety of the alkyl glycolate). These reactions are of two general types, viz., those which reverse when heated and those which are thermally irreversible. Examples of these two reactions are:

Thermally reversible

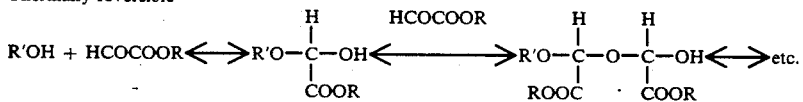

Thermally irreversible $$HCOCOOR + R'OH \longrightarrow HCOCOOR' + ROH$$

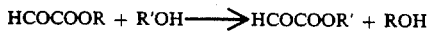

The thermally reversible reactions produce families of nonvolatile polymeric hemiacetals that can be decomposed to the monomeric species by the addition of heat. The irreversible reactions represent a permanent loss of product. Therefore, isolation of the glyoxylate by simple distillation is impossible, although more complex schemes can be successfully employed.

A typical reaction mass contains more total alkyl glycolate, water and the alkanol corresponding to the alkyl glycolate, on a molar basis, than alkyl glyoxylate. Because there are more impurities than alkyl glyoxylate, the bulk of the glyoxylate will be involved in the thermally reversible and irreversible reactions. If the amount of impurities is reduced, the interactions between the alkyl glyoxylate and the other reaction constituents will be reduced, and the alkyl glyoxylate can be more easily recovered. If no water or alcohol were present, there would be no thermally reversible or irreversible reactions with water or alcohol, although the reactions between the alkyl glycolate and alkyl glyoxylate would still occur. To maximize the production of free alkyl glyoxylate, methods have been sought to reduce the amount of water and alcohol, as well as the amount of alkyl glycolate. In the past, decreasing the content of the water and the alcohol corresponding to the alkyl glycolate has been achieved by distillation or by adding a species that reacts with or azeotropes the water and alcohol. The amount of alkyl glycolate remaining in the reaction mass can be minimized by achieving higher reactor conversions.

U.S. Pat. No. 4,502,923 discloses a method to isolate alkyl glyoxylate from its impurities in a series of distillations. A low boiling azeotroping agent is introduced to cause water and alcohol to distill overhead. The water and alcohol content is then lowered by a vacuum distillation. The residue from the first column is distilled in a second column to decrease the ratio of alkyl glycolate to alkyl glyoxylate. The residue of the second column is then distilled at a higher pressure in a third column to recover the high purity alkyl glyoxylate as a side draw. To produce high purity alkyl glyoxylate in the prior art process, it is necessary to have a large recycle stream on the order of 11 lbs. of recycle throughout the three distillation columns per pound of product takeoff. Consequently, the capital investment in plant equipment is high, while the production of product is low.

Australian Patent No. 30007 -84 discloses a method for isolation of the glyoxylic ester from materials co-formed during an oxidative dehydrogenation of an alkyl glycolate. Immediately after leaving the reactor, the gaseous reaction mixture is quenched with a low-boiling entrainer, such as a hydrocarbon, having a lower boiling point than the glyoxylic ester. The entrainer is used to azeotropically distill water and alcohol. The reaction mixture, along with the entrainer, is passed to a fractionating column, where the water azeotrope and other low boilers are taken overhead while the glyoxylic ester is taken off as bottoms. The method has the disadvantage that some of the water and alcohol in the reaction mixture forms high-boiling hemiacetals and hydrates before they can be azeotropically distilled, requiring the use of additional steps to produce high purity alkyl glyoxylate.

It is also known that high purity alkyl glyoxylate can be isolated from a mixture containing alkyl glyoxylate, water, and alcohol in combined form by distillation from phosphorous pentoxide [W. Oroshnik and P. E. Spoerri, J. Amer. Chem. Soc. 1941, 63,3338 and J. M. Hook, Synthetic Communications, 14(1), 83–87 (1984)]. Product losses are high and a highly corrosive waste stream is formed, which poses difficult disposal problems. In addition, the reaction with $P_2O_5$ is extremely exothermic. Consequently, this technique is suitable only for small-scale operations.

A simple and cost-effective method to isolate alkyl glyoxylate is desired. If an economical method were developed which minimized the contact between the alkyl glyoxylate and the various hydroxyl groups, the thermally reversible and irreversible reactions could be inhibited and product isolation improved.

OBJECTS OF THE INVENTION

A principal object of the invention is to provide an improved process for purifying alkyl glyoxylate without using complicated multiple distillation schemes.

Another object of the invention is to provide a process for purifying alkyl glyoxylate which minimizes the production of its hemiacetals and hydrates.

Still another object is to provide a method of purifying alkyl glyoxylate which avoids the use of costly agents and highly corrosive waste streams.

Upon further study of the specification and appended claims, further objects and advantages of this invention will become apparent to those skilled in the art.

SUMMARY OF THE INVENTION

A process is provided for the isolation of high purity alkyl glyoxylate from a catalyzed gas phase oxidative dehydrogenation of an alkyl glycolate to form a resultant gaseous reaction mixture containing alkyl glyoxylate, alkyl glycolate, water, alkanol, and reaction by-products, which comprises using a solvent to selectively remove the alkyl glyoxylate and alkyl glycolate from the reaction mixture and removing the alkyl glycolate by distillation by: reducing the water and alkanol content of the reaction mixture by contacting the gaseous reaction mixture with a hot solvent which is immiscible with water, which selectively dissolves substantially only the alkyl glyoxylate and alkyl glycolate to form a solution thereof, which has a boiling point above the boiling point of the solution containing alkyl glycolate and below the temperature at which the alkyl glyoxylate degrades, and which permits the separation of water and alkanol to be removed in the vapor stage, thereby minimizing the thermally reversible and irreversible reactions. The high purity alkyl glyoxylate is then removed from the solution by distillation to provide as the residue a mixture consisting essentially only of solvent and alkyl glycolate. In practice, the residual mixture can then be distilled to separate the alkyl glycolate, and solvent is thus recovered from the bottoms.

In a preferred aspect, the present invention provides an improved process for the preparation of high purity alkyl glyoxylate at temperatures below which degradation of the alkyl glyoxylate occurs, wherein the gaseous reaction mixture is first contacted with liquid bottoms from the packed isolation column; the gaseous reaction mixture is then introduced into the isolation column countercurrent to a hot nitrobenzene solvent; water and alcohol vapors at a temperature of from about 60°–100° C. are removed overhead from the packed isolation column; and the bottoms in the isolation column are maintained at a temperature of from about 100°–150° C.

DETAILED DESCRIPTION OF THE INVENTION

A method has been developed whereby an alkyl glyoxylate and the alkyl glycolate from which it is produced can be separated from the lower boiling impurities formed in the oxidative dehydrogenation reaction of alkyl glycolate. According to the process of the present invention, the reaction mixture produced by the gaseous state oxidation of an alkyl glycolate is contacted with at least one solvent, which forms a solution by selectively dissolving only the alkyl glycolate and alkyl glyoxylate and allowing the water and alcohol to be removed in the vapor state, thereby minimizing the thermally reversible and irreversible reactions which form undesired hemiacetals and hydrates. The solvent was also found to stabilize the product against thermally reversible and irreversible reactions and degradation of the product. Thus, the reaction mixture can be heated to a higher temperature without loss of product. Another benefit of the invention is that the solvent stabilizes the product against thermally irreversible reactions and degradation. Because of this increased stability, the alkyl glyoxylate solution can be stored for longer periods of time without degradation.

Suitable solvents for use in this invention are those which are immiscible with water, which selectively dissolve the alkyl glyoxylate and alkyl glycolate, and which preferably have a boiling point above that of the solution containing the alkyl glyoxylate and below the temperature at which degradation of the alkyl glyoxylate occurs. The solvent also has the characteristic that it is possible to separate the water and other organics from the multi-component solution and recover the purified alkyl glyoxylate. Preferably, the solvent is contacted with the gaseous reaction mixture at a temperature of from 70° to 130° C.

Although any solvent which satisfies these criteria can be used, preferred solvents are ortho-dichlorobenzene, nitrobenzene, tetrabutyl urea, poly(tetramethylene ether)glycol, adiponitrile, and tributyl phosphate, with nitrobenzene being most preferred. One or more of these or other suitable solvents may be used in combination to achieve the desired separation.

According to a preferred embodiment of the present invention, a column is used which provides sufficient contact between the solvent and the gaseous reaction effluent so that the alkyl glycolate and alkyl glyoxylate can be preferentially dissolved and removed and thermally reversible and irreversible reactions minimized. Conventional columns, such as a packed distillation column, may be employed to maximize the contact between the solvent and the reaction constituents. The packing material is preferably formed of a glass or ceramic material and is shaped to provide a large surface area, thereby maximizing the gas-liquid contact. The column is preferably configured for countercurrent flow of the solvent and gaseous reaction mass. Although the column can be placed in any position, a vertical column is preferred in which the solvent enters at or near the top of the columns, and the gaseous reaction mixture is introduced at or near the bottom of the column.

The gaseous reaction mass may also be bubbled through a column filled with a solvent so that water and alcohol are removed overhead as vapors. In another preferred embodiment, the gaseous reaction mass is passed into a spray tower with the solvent being sprayed in fine droplets to maximize gas-liquid contact with the solution of the alkyl glyoxylate and alkyl glycolate.

The alkyl glycolate used as a starting material in the oxidative dehydrogenation reaction can be prepared by the esterification of glycolic acid with an aliphatic alcohol. The aliphatic alcohol preferably contains from 1 to 6 carbon atoms. Methanol is particularly preferred. Methods to produce the alkyl glyoxylate from the alkyl glycolate are described in U.S. Pat. No. 4,340,748 and European Patent No. 149,439. It is preferred that the methods described in co-pending patent applicaton Ser. Nos. 07/417,653, now U.S. Pat. No. 5,126,478 and 07/417,651 now abandoned are used in the preparation of the alkyl glyoxylate. The high purity alkyl glyoxylate produced from the alkyl glycolate and separated by the process of the present invention can be used in the synthesis of a variety of chemical compounds, including pharmaceuticals.

The gaseous reaction mixture from the oxidative dehydrogenation reaction of the alkyl glyoxylate is preferably rapidly cooled to minimize product loss before being dissolved in the solvent. In a preferred embodiment, the gaseous reaction mixture is cooled to a temperature near its dew point, more preferably in the range of from about 150° to 175° C. The gaseous reaction constituents may be cooled externally in a conventional heat exchanger or internally inside the isolation column.

Although the temperature profile of the column will vary somewhat, depending upon the particular solvent or solvent combinations utilized, it is important to operate the isolation column with a temperature profile permitting removal from the column of the water and alcohol in the vapor phase.

The temperature of the gas-liquid mixture at the top of the isolation column is preferably in the range of from about 60° to 100° C., and the bottom temperature preferably ranges from about 100° to 150° C. In a preferred aspect of the present invention using a nitrobenzene solvent, the isolation column is operated with a top temperature of about 70° C., and a bottom temperature ranging from about 135° to 140° C. By operation of the isolation column with the above-described temperature profile, the water and/or alcohol can be removed as vapors from the top of the column.

In a preferred aspect of the invention, the separation is optimized by immediately contacting the gaseous reactor effluent with liquid bottoms from the isolation column. One method of achieving this intimate contact is by spraying liquid bottoms from the isolation column into the gaseous effluent as it is discharged from the reactor. Another method of achieving the same effect is to introduce the gaseous effluent from the reactor directly into the liquid bottoms of the isolation column.

The ratio of solvent to gaseous reactor effluent preferably ranges from about 1:1 to 10:1 on a weight basis. In a preferred embodiment, the ratio of 2 parts of solvent per part of reactor effluent is used. This includes the solvent which is recycled to the isolation column from the distillation of the bottoms from the isolation column.

The bottoms of the isolation column, which consist mainly of alkyl glycolate, alkyl glyoxylate and solvent, are preferably separated in two conventional distillation columns in which the solvent and glycolate are separated from the glyoxylate in the first column. Then the solvent is separated from the glycolate in a second column and returned to the top of the isolation column. The overhead from the second column containing alkyl glycolate can be recycled back to the reactor and used to supplement the feed stock.

In a preferred embodiment, the solvent is selected from the group consisting of ortho-dichlorobenzene, nitrobenzene, tetrabutyl urea, poly(tetramethylene ether)glycol, adiponitrile, and tributyl phosphate, wherein the gaseous reaction mixture is cooled to a temperature of from about 150°-175° C. before being introduced into the isolation column; wherein the ratio of solvent to gaseous reaction mixture is from about 1:1 to 10:1 dry weight; and wherein the alkyl moiety of the alkyl glyoxylate, alkyl glycolate and alkanol contains from 1 to 6 carbon atoms and is preferably methyl.

The process of this invention preferably comprises:

(a) a stream of the gaseous reaction mixture and a stream of the hot solvent are introduced into an isolation column in a countercurrent manner;

(b) a stream of water and alkanol in the vapor phase is removed from the overhead of the isolation column;

(c) a stream of the bottoms of the isolation column is introduced into a first fractionating column wherein the alkyl glyoxylate is removed therefrom by distillation to provide a residue mixture of alkyl glycolate and solvent;

(d) a stream of the residue mixture is introduced into a second fractionating column wherein the alkyl glycolate is distilled therefrom; and (e) recovering solvent from the bottoms of the second fractionating column.

In this preferred aspect of the process of this invention, the bottoms of the isolation column are at a temperature of about 135°-140° C.; the ratio of the solvent to gaseous reaction mixture is about 2:1; the water and alcohol vapors from the overhead of the isolation column are at a temperature of about 70° C.; the pressure in the isolation column is from about 1 to 10 psia; the solvent entering the isolation column is at a temperature of from about 60° to 100° C.; and the gaseous reaction mixture is contacted with liquid bottoms from the isolation column before being introduced into the isolation column.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperaturs are set forth uncorrected in degrees Celsius and, unless otherwise indicated, all parts and percentages are by weight.

The entire text of all applications, patents and publications, if any, cited above and below are hereby incorporated by reference.

EXAMPLE 1

This Example illustrates the separation of alkyl glyoxylate and alkyl glycolate from water and lower alcohol co-formed when alkyl glycolate is oxidatively dehydrogenated to form alkyl glyoxylate.

A vapor mixture at 250°±4° C. of methyl glycolate (MGL) (100 g/hr), oxygen as air (at 0.6 equivalents of $O_2$/MGL) and 48% excess $N_2$ (relative to the $N_2$ in the air) was passed through a ½"-I.D. quartz U-shaped tube containing a ¼"-long bed of silver needles located near the discharge side of the tube. The reactor was suspended in a heating fluidized sand bath to control/maintain the catalyst operating temperature at 476° C. At this temperature, 59% of the MGL was converted to methyl glyoxylate (MGX) with a selectivity of 89%. The reactor product stream was then passed up through a three-stage counter-current scrubber column, wherein nitrobenzene solvent at 1.8 g/min. was passed down the temperature staged columns. The temperature was such that the MGL and MGX were scrubbed by the nitrobenzene solvent from the product vapor stream and the more volatile water and methanol in the vapor passed through the column and were discharged overhead. The dissolved MGX and unreacted MGL were collected in a receiver at the bottom of the column. The receiver was maintained at about 149° C. The top of the three-stage packed column was maintained at 77° C. and the bottom at 134° C. The product was removed from the receiver based on receiver level and was immediately cooled. Seventy-two percent of the MGX was recovered from the reactor product stream. These results, along with the data from four other examples, are shown in Table 1, below.

TABLE 1

| Run No. | R × T °C. | 02/MGL Equiv. | N2 % xs | Conv. % | Sel. % | Yld. % | NB g/min | Rblr/Cbt/Ctp °C. | MGX % Rc |
|---|---|---|---|---|---|---|---|---|---|
| 1 | 476 | 0.58 | 48 | 59 | 89 | 53 | 1.8 | 149/134/77 | 72 |
| 2 | 475 | 0.60 | 48 | 74 | 78 | 57 | 2.3 | 142/122/71 | 84 |
| 3 | 475 | 0.58 | 48 | 69 | 82 | 56 | 2.1 | 148/131/78 | 76 |
| 4 | 474 | 0.64 | 46 | 78 | 71 | 56 | 1.9 | 143/126/77 | 83 |
| 5 | 471 | 0.75 | 41 | 95 | 56 | 53 | 1.9 | 143/129/78 | 55 |

R × T = Catalyst Operative Temperature
N2 % xs = % excess nitrogen
Conv. = Conversion
Sel. = Selectivity
NB = Nitrobenzene
Rblr/Cbt/Ctp = Receiver temp/Column bottom temp/ Column top temp.
MGX = methyl glyoxalate

EXAMPLE 2

This Example illustrates the separation of alkyl glyoxylate and alkyl glycolate from water and lower alcohols co-formed when alkyl glycolate is oxidatively dehydrogenated to form alkyl glyoxylate.

Oxidative dehydrogenation of methyl glycolate (MGL) to methyl glyoxylate is carried out in two 10 mm diameter quartz reactors, connected in series, each of which contains a 1" bed (8 grams) of silver crystals. The MGL is fed to a vaporizer where it is mixed with 450 sccm oxygen and some nitrogen diluent (total 02/N2 ratio is 850/200 sccm). This reaction stream is heated to 150°–160° C. to vaporize the MGL. The gaseous stream is then passed over the first catalyst bed which is externally heated to 400° C. to initiate reaction. The reaction product stream exits the catalyst bed at a temperature of about 475° C. and is cooled to about 160° C. by applying cryogenic cooling to the exit end of the reactor. This product stream is then mixed with additional oxygen and passed into the second reactor also containing a 1" bed of silver crystals and heated externally to 400° C. where more of the MGL is oxidized to methyl glyoxylate. The product stream from the second reactor is again at about 475° C. and is cooled cryogenically to about 160° C.

The effluent stream from the second reactor is fed between the fourth and fifth unit of six scrubber sections each of which is held at a given temperature with the lowest at the top scrubber and the highest at the bottom scrubber with the range being 66 to 132. When the top scrubber section is below ≈80° C. (examples 1 and 2) more hydrolysis of the ester occurs than when the lowest temperature is ≈90 (examples 4 & 5). However, as scrubber temperatures are increased more of the MGX is lost overhead.

TABLE 2

| Run No. | Scrubber Temperatures | | | | | | % MGX | | | |
|---|---|---|---|---|---|---|---|---|---|---|
| | 1 | 2 | 3 | 4 | 5 | 6 | % Con | % Sel | % rec. | % FA* |
| 1 | 66 | 70 | 80 | 91 | 131 | 130 | 79.9 | 45.1 | 98.9 | 2.48 |
| 2 | 70 | 81 | 90 | 119 | 133 | 132 | 82.5 | 42.2 | 98.0 | 0.74 |
| 3 | 82 | 90 | 100 | 113 | 115* | 132 | 73.3 | 63.8 | 96.6 | 0.41 |
| 4 | 91 | 93 | 102 | 110 | 119 | 121 | 79.3 | 48.4 | 82.0 | 0.19 |
| 5 | 94 | 98 | 101 | 110 | 119 | 130 | 79.0 | 53.9 | 77.6 | 0.17 |

*FA = Free Acid

EXAMPLE 3

This example illustrates the separation of high purity alkyl glyoxylate from a mixture of alkyl glycolate, alkyl glyoxylate, and solvent obtained as the non-volatile residue from the column operation described in the first two examples.

The residue from the distillation column described in Examples 1 and 2 was fed at a rate of 6–8 g/min to the 13th plate of a one-inch diameter Oldershaw column containing 40 distillation plates. The column pressure was maintained at 225 torr and the temperature at the bottom of the column was held at 140°–150° C. The heat input was adjusted to get a reflux ratio of 5:1. After allowing from 1–2 hours for equilibrium to be established, the product withdrawn from the top of the Oldershaw column was shown to be 99+% pure methyl glyoxylate by gas chromatographic analysis. The residue collected at the bottom of the column was shown by gas chromatographic analysis to be essentially a binary mixture of 93+% nitrobenzene and 6% methyl glycolate. Separation of this mixture into individual components can be accomplished by standard techniques well known to those skilled in the art, such as, for example, by distillation.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. In a process for the isolation of high purity alkyl glyoxylate from a catalyzed gas phase oxidative dehydrogenation of an alkyl glycolate to form a resultant gaseous reaction mixture containing alkyl glyoxylate, alkyl glycolate, water, alkanol, and reaction by-products, the improvement which comprises using a solvent to selectively remove the alkyl glyoxylate and alkyl glycolate from the reaction mixture and recovering the alkyl glyoxylate by distillation by:

(a) reducing the water and alkanol content of the reaction mixture by contacting the gaseous reaction mixture with a hot solvent which is immiscible with water, and which forms a solution by selectively dissolving substantially the alkyl glyoxylate and alkyl glycolate, which has a boiling point above the boiling point of the solution containing alkyl glyoxylate and below the temperature at which the alkyl glyoxylate degrades, and which permits the separation of water and alkanol from the solution;

(b) removing high purity alkyl glyoxylate by distilling the solution from step (a) to provide a residue mixture consisting essentially of solvent and alkyl glycolate; and (c) distilling the alkyl glycolate from the distillation residue from step (b) and recovering the thus-isolated solvent from the distillation residue.

2. The process of claim 1, wherein the ratio of solvent to gaseous reaction mixture in step (a) is from about 1:1 to 10:1 by weight.

3. The process of claim 1, wherein the alkyl moiety of the alkyl glyoxylate, alkyl glycolate and alkanol contains from 1 to 6 carbon atoms.

4. The process of claim 3, wherein the alkyl moiety is methyl.

5. The process of claim 1, wherein the solvent is selected from the group consisting of ortho-dichlorobenzene, nitrobenzene, tetrabutyl urea, poly(tetramethylene ether)glycol, adiponitrile, and tributyl phosphate.

6. The process of claim 1, wherein the gaseous reaction mixture from the catalyzed gas phase oxidative dehydrogenation is cooled to a temperature of about 150°–175° C. before contact with the solvent.

7. The process of claim 1, wherein the gaseous reaction mixture contains an inert gas.

8. The process of claim 1, wherein the solvent is contacted with the gaseous reaction mixture at a temperature of from 70° to 130° C.

9. The process of claim 1, wherein steps (a), (b) and (c) are accomplished by:

(i) introducing the resultant gaseous reaction mixture and the hot solvent into an isolation column in a countercurrent manner whereby a vapor phase comprising water and alkanol is formed which passes to the top of the column and a liquid phase is formed which passes to the bottom of the column;

(ii) removing the vapor phase from the top of the isolation column;

(iii) removing the liquid from the bottom of the isolation column and introducing it into a first fractionating column wherein high purity alkyl glyoxylate is removed therefrom by distillation leaving behind a residue mixture of alkyl glycolate and solvent;

(iv) introducing the residue mixture into a second fractionating column wherein the alkyl glycolate is distilled therefrom leaving behind a residue mixture comprising solvent; and (v) recovering the solvent from the second fractionating column.

10. The process of claim 9, wherein the solvent is selected from the group consisting of ortho-dichlorobenzene, nitrobenzene, tetrabutyl urea, poly(tetramethylene ether)glycol, adiponitrile, and tributyl phosphate, wherein the gaseous reaction mixture is cooled to a temperature of from about 150°–175° C. before being introduced into the isolation column; wherein the ratio of solvent to gaseous reaction mixture is from about 1:1 to 10:1 dry weight; and wherein the alkyl moiety of the alkyl glyoxylate, alkyl glycolate and alkanol contains from 1 to 6 carbon atoms.

11. The process of claim 10, wherein the alkyl moiety is methyl.

12. The process of claim 9, wherein the gaseous reaction mixture is contacted with liquid bottoms from the isolation column before being introduced into the isolation column.

13. The process of claim 9, wherein the gaseous reaction mixture is introduced into the bottom of the isolation column and passes upwardly countercurrent with respect to the solvent in the isolation column.

14. The process of claim 9, wherein the liquid in the bottom of the isolation column is maintained at a temperature of from about 100°–150° C.

15. The process of claim 9, wherein water and alkanol vapors discharge from the top of the isolation column at a temperature of from about 60°–100° C.

16. The process of claim 9, wherein the isolation column is a packed column.

17. The process of claim 9, wherein the solvent recovered as distillate in the second fractionating column is recycled to the isolation column.

18. The process of claim 9, wherein alkyl glycolate from the second fractionating column is recycled to a reactor where it is oxidatively dehydrogenated to form additional alkyl glyoxylate.

19. An improved process for the isolation of high purity methyl glyoxylate from the reaction mixture obtained from the catalyzed gas phase oxidative dehydrogenation of methyl glycolate to form a gaseous reaction mixture containing methyl glyoxylate, methyl glycolate, water, methyl alcohol, and miscellaneous impurities, wherein the improvement comprises:

(a) reducing the water and methyl alcohol content of the gaseous reaction mixture by passing it through a packed isolation column countercurrent to a hot solvent selected from the group consisting of ortho-dichlorobenzene, nitrobenzene, tetrabutyl urea, poly(tetramethylene ether) glycol, adiponitrile, and tributyl phosphate to form a vapor phase comprising water and methyl alcohol and a liquid residue;

(b) removing the water and methyl alcohol vapor phase which passes overhead of the isolation column at a temperature of from about 60°–100° C.;

(c) removing high purity methyl glyoxylate from the liquid residue of the isolation column by distillation in a first fractionating column which yields a second residue mixture of methyl glycolate and solvent; and (d) distilling the second residue mixture in a second fractionating column to form a vapor phase comprising methyl glycolate and a liquid residue comprising solvent, and recovering the solvent from the residue.

20. The process of claim 19, wherein the residue from the isolation column is at a temperature of about 130°–140° C.; wherein the ratio of the solvent to gaseous reaction mixture is about 1:1 by weight, wherein the water and methyl alcohol vapors from the overhead of the isolation column are at a temperature of about 70° C.; wherein the pressure in the isolation column is from about 1 to 10 psia; wherein the solvent entering the isolation column is at a temperature of from about 60° to 100° C.; and wherein the gaseous reaction mixture is contacted with liquid residue from the isolation column before being introduced into the isolation column.

* * * * *